(12) United States Patent
Zhao et al.

(10) Patent No.: US 8,492,523 B2
(45) Date of Patent: Jul. 23, 2013

(54) DRAGLINE PROTEIN

(75) Inventors: Tianfu Zhao, Kitakatsuragi-gun (JP); Yujun Wang, Kitakatsuragi-gun (JP); Masao Nakagaki, Ueda (JP)

(73) Assignee: Okamoto Corporation, Nara (JP)

( * ) Notice: Subject to any disclaimer, the term of this patent is extended or adjusted under 35 U.S.C. 154(b) by 20 days.

(21) Appl. No.: 13/226,157

(22) Filed: Sep. 6, 2011

(65) Prior Publication Data

US 2012/0065372 A1    Mar. 15, 2012

(30) Foreign Application Priority Data

Sep. 10, 2010    (JP) .................................. 2010-203556

(51) Int. Cl.
*A61K 38/17*    (2006.01)

(52) U.S. Cl.
USPC ........................................................ 530/353

(58) Field of Classification Search
None
See application file for complete search history.

(56) References Cited

FOREIGN PATENT DOCUMENTS

| WO | WO 02/099082 A2 | 12/2002 |
| WO | WO 03/020916 A2 | 3/2003 |
| WO | WO 2006/008163 A2 | 1/2006 |

OTHER PUBLICATIONS

Nadia A. Ayoub et al., "Blueprint for a High-Performance Biomaterial: Full-Length Spider Dragline Silk Genes," Issue6,e514, 2007, p. 1-13.
William A. Gaines IV et al., "Identification and Characterization of Multiple Spidroin 1 Genes Encoding Major Ampullate Silk Proteins in *Nephila clavipes*," Insect Mol. Biol, Sep. 2008, vol. 17, No. 5.
P. Tijssen, "Laboratory Techniques in Biochemistry and Molecular Biology-Hybridization with Nucleic Acid Probes Part I, Chapter 2," Overview of principles of hybridization and the strategy of nucleic acid probe assays, Hybridization and Nucleic Acid Probe Assays, 1993, p. 1-78.
Cheryl Y. Hayashi et al., "Evidence from Flagelliform Silk cDNA for the Structural Basis of Elasticity and Modular Nature of Spider Silks," J. Mol. Biol., 1998, p. 773-784, vol. 275.
Thomas Scheibel, "Spider silks: recombinant synthesis, assembly, spinning and engineering of synthetic proteins," Microbial Cell Factories, 2004, p. 1-10, vol. 3, No. 14.
Glareh Askarieh et al., "Self-Assembly of Spider Silk Proteins is Controlled by a pH-sensitive Relay", Nature, May 2010, p. 236-239, vol. 465.
J. M. Gosline et al., "The Mechanical Design of Spider Silks: From Fibroin Sequence to Mechanical Function", The Journal of Experimental Biology, 1999, pp. 3295-3303, vol. 202.
European Patent Office, European Search Report issued in corresponding EP Application No. 11180489.4, dated Nov. 10, 2011.
Du et al., "Design of Superior Spider Silk: From Nanostructure to Mechanical Properties," Biophysical Journal, 2006, vol. 91, No. 12, pp. 4528-4535.
Keten et al., "Nanostructure and Molecular Mechanics of Spider Dragline Silk Protein Assemblies," J. R. Soc. Interface, 2010, vol. 7, No. 53, pp. 1709-1721.
Sheu et al., "Lattice Deformation and Thermal Stability of Crystals in Spider Silk," International Journal of Biological Macromolecules, 2004, vol. 34, No. 5, pp. 267-273.
Tso et al., "Giant Wood Spider *Nephila pilipes* Alters Silk Protein in Response to Prey Variation," The Journal of Experimental Biology, 2005, vol. 208, No. 6, pp. 1053-1061.
Wen et al., "Transgenic Silkworms (*Bombyx mori*) Produce Recombinant Spider Dragline Silk in Cocoons," Mo. Biol. Rep., 2009, vol. 37, No. 4, pp. 1815-1821.
Zhao et al.,"New and Highly Efficient Expression Systems for Expressing Selectively Foreign Protein in the Silk Glands of Transgenic Silkworm," Transgenic Res., 2009, vol. 19, No. 1, pp. 29-44.

*Primary Examiner* — Suzannne M Noakes
(74) *Attorney, Agent, or Firm* — Sughrue Mion, PLLC

(57) ABSTRACT

To provide a new natural fiber material with excellent physical properties. Any one of the following nucleic acids (a) to (d): (a) a nucleic acid having a base sequence of SEQ ID NO: 1 or 19; (b) a nucleic acid encoding a protein having an amino acid sequence of SEQ ID NO: 2 or 20; (c) a nucleic acid encoding a dragline protein and having a sequence identity of 90% or more with the nucleic acid (a); (d) a nucleic acid which encodes a dragline protein and hybridizes with a complementary chain of the nucleic acid (a) under stringent conditions.

5 Claims, 5 Drawing Sheets

Fig.1

```
  1  GGGGGATATG GAGCAGGAAG TGGATCTACC ATCGCAATAA CTGCTGGTGG
 51  TCTTGGTGGA TCTGGAGGTC AAGGTGGCCA AATACCATCT GGCGCTGTTG
101  GACAAGGAAC TCAAGGATAT GGAACAGGAA GTGGAGCAAC CATCGCATTA
151  ACTGCTGGTG GACTTGGGGG ACAAGGTGGT CAAGGACCAT CTGGCTCTGG
201  TGGACAAGGC CCATCAGGAC AAGGAGCTCA AGGACCTGGC GGATATGGAG
251  CAGGAAATGC AGCCGCCGCC AACGCAGCAG CTAGTGGACT TGGAGGCTAT
301  GGAGTTGGTG GGCAGGGAAG TGGCCAAAGA CCATCTGGAG CTGGTGGACA
351  AGGTGCTCAA GCGCCAGGTG GATATGGAAC AGGAAGTGGA TCGACCATCG
401  TAATAACTGC TGGTGGACAG AGAGGACAAG GTGGTCAAGG ACCATCAGGA
451  CAATTAGCTC AAGCACCTAG TGGATATGGA CAAGGAAGTG GAGCCGCCGC
501  CGCCTCTGGT GGTCTTGGAG GATATGGAGG TCAAGGTGGC AAAGATCAT
551  CTGGCGCTGG TGCACAAGGA ACTCAAGGAT ATGGTACAGG AAGTGGAACA
601  ACTATCGCAT TAACTGCTGG TGGTATTGGA GGATCTGGAG GTCAAGGTGG
651  CCAAAGACCA TCTGGCATTG GTGGACAAGG AGCTCAAGGG CCAGGTGGAT
701  ATGGAGCAGG AAGTGGATCT ACCATCGCAA TAACTACTGG TGGTCTTGGT
751  GGATATGGAG GTCAAGGTGG CCAAAGACCA TCTGGCGCTG ATGGACAAGG
801  AGCTCAAGGA TATGGAACAG GAAGTGGAGC TACCATCGCT TTAACTGCTG
851  GTGGACTTGG AGGTTATGGT GGACAGAGAG GTCAAGTTGG TCAAGGACCA
901  TCAGGACAAT TAGCTGGAGC ACCTGGTGGA TATGGACAAG GAAGTGCAGC
951  CGCCACGGCA GCTGGTGGAC TTCGAGGTTT CGGGCAAGGG TTACAAGTAC
```

Fig.2

| α | V | β |
|---|---|---|
| GGLGGSGGQGG | QIPSGAVGQGTQGYGTGSG | ATIALTA |
| GGLGGQGGQGP | SGSGGQGPSGQGAQGPGGYGAG | NAAAANAAA |
| SGLGGYGVGGQGSGQRPSGAGGQGAQAPGGYGTGSGS | | TIVITA |
| GGQRGQGGQGP | SGQLAQAPSGYGQGSG | AAAAS |
| GGLGGYGGQGG | QRSSGAGAQGTQGYGTGSG | TTIALTA |
| GGIGGSGGQGG | QRPSGIGGQGAQGPGGYGAGSGS | TIAITT |
| GGLGGYGGQGG | QRPSGADGQGAQGYGTGSG | ATIALTA |
| GGLGGYGGQRGQVGQGPSGQLAGAPGGYGQGS | | AAATAA |

Fig.4

| | | | | | |
|---|---|---|---|---|---|
| 1 | GGTGGTCTTG | GTGGATATGG | AGGTCAAGGT | GGCCAAAGAC | TATCTGGCGC |
| 51 | TAGTGGACAA | GGAACTCAAG | GATATGGAAC | AGGAAGTGGA | GCTACCATCG |
| 101 | CTTTAACTGC | TGGTGGTCAA | GGTGGATCTG | GAGGTCAAGG | TGGCCAAAGA |
| 151 | CTATCTGGCG | CTAGTGGACA | AGGAACTCAA | GGATATGGAA | CAGGAAGTGG |
| 201 | AGCAACCATC | GCATTAACTG | CTGGTGGACT | TGGGGGACAA | GGTGGTCAAG |
| 251 | GACCATCTGG | CTCTGGTGGA | CAAGGCCCAT | CAGGACAAGG | AGCTCAAGGG |
| 301 | CCAGGTGGAT | ATGGAACAGG | AAGTGGAACG | GCCATCGCAA | TAACTGCTGG |
| 351 | TGGACAGAGA | GGACAAGGTG | GTCAAGGACC | ATCAGGACAA | TTAGCTCAAG |
| 401 | CACCTAGTGG | ATATGGACTA | GGAAGTGGAG | CCGCCGCCGC | CTTTGGTGGT |
| 451 | CTTGGAGGAT | ATGGAGGTCA | AGGTGGCCAA | AGATCATCTG | GCGCTGGTGC |
| 501 | ACAAGGAACT | CAAGGATATG | GAACAGGAAG | TGGAACAACT | ATCGCATTAA |
| 551 | CTGCTGGTGG | TATTGGAGGA | TCTGGAGGTC | AAGGTGGCCA | AAGACCATCT |
| 601 | GGCGCTGGTG | GACAAGGAGC | TCAAGGGCCA | GGTGGATATG | GAGCAGGAAG |
| 651 | TGGATCTACC | ATCGCAATAA | CAGCTGGTGG | TCTTGGTGGA | TCTGCAGGTC |
| 701 | AAGGTGGCCA | AAGACCATCT | GGCGCTGGTG | GACAAGGAGC | TCAAGGATAT |
| 751 | GGAACAGGAA | GTGGAGCTAC | CATCGCAATA | ACTGCTGGTG | GACTTGGAGG |
| 801 | TTATGGTGGA | CAGAGAGGTC | AAGTTGGTCA | AGGACCATCA | GGACAATTAG |
| 851 | CTGGAGCACC | TGGTGGATAT | GGACAAGGAA | GTGCAGCCGC | CACGGCAGCT |

Fig.5

```
         α                      V                         β
┌─────────────────────────────────────────────────────┬─────────┐
GGLGGYGGQGGQRLSGASGQGTQGYGTGSG                        ATIALTA
GGQGGSGGQGGQRLSGASGQGTQGYGTGSG                        ATIALTA
GGLGGQGGQGPSGSGGQGPSGQGAQGPGGYGTGSG                   TAIAITA
GGQRGQGGQGPSGQLAQAPSGYGLGSG                             AAAAF
GGLGGYGGQGGQRSSGAGAQGTQGYGTGSG                        TTIALTA
GGIGGSGGQGGQRPSGAGGQGAQGPGGYGAGSGS                     TIAITA
GGLGGSGGQGGQRPSGAGGQGAQGYGTGSG                        ATIAITA
GGLGGYGGQRGQVGQGPSGQLAGAPGGYGQGS                       AAATAA
```

DRAGLINE PROTEIN

BACKGROUND OF THE INVENTION

1. Field of the Invention

The present invention relates to a nucleic acid, a protein encoded by the nucleic acid, a recombinant organism having the nucleic acid introduced therein and a protein produced by the recombinant organism.

2. Related Background Art

A spider silk is known as a naturally occurring high performance polymer with excellent toughness due to a combination of strength and elasticity. A spider has at most 7 specialized glands, from which many types of spider silk different in nature are produced, and among them, attention has been focused on a dragline produced by Major Ampullate as the toughest spider silk in the development of new materials used in various industrial fields such as medical, aviation and apparel industries.

A protein called Major Ampullate Spidroin (MaSp) is known as a major protein constituting a dragline, and up to now, gene sequences encoding MaSp proteins of various spiders such as *Latrodectus hesperus, Latrodectus geometricus* and *Nephila clavipes* have been elucidated (Non-Patent Literature 1: Nadia A. Ayoub et al., Blueprint for a High-Performance Biomaterial: Full-Length Spider Dragline Silk Genes, 2007, Issue 6, e514; Non-Patent Literature 2: William A. Gaines IV et al., Identification and Characterization of Multiple Spidroin 1 Genes Encoding Major Ampullate Silk Proteins in *Nephila clavipes*, Insect Mol Biol, 2008, 17(5), 465-474; and so on.).

SUMMARY OF THE INVENTION

However, in each of the industrial fields, demand for a natural fiber with excellent physical properties is increasing more and more and further development of new materials have been expected.

Then, the present invention aims to provide a material with excellent physical properties for a natural fiber.

The present inventors intensively studied with a view to achieving the aforementioned aims, as a result, found that a gene encoding an MaSp protein constituting a dragline of *Nephila pillipes* has a unique structure different from MaSp genes conventionally known, and thereby completed the present invention.

Thus, the present invention relates to (1) any one of the following nucleic acids (a) to (d):

(a) a nucleic acid having a base sequence of SEQ ID NO: 1 or 19;

(b) a nucleic acid encoding a protein having an amino acid sequence of SEQ ID NO: 2 or 20;

(c) a nucleic acid encoding a dragline protein and having a sequence identity of 90% or more with the nucleic acid (a);

(d) a nucleic acid which encodes a dragline protein and hybridizes with a complementary chain of the nucleic acid (a) under stringent conditions.

Furthermore, the present invention relates to (2) a nucleic acid encoding a dragline protein, comprising any one of the following nucleic acids (e) to (h) and having a sequence identity of 70% or more, preferably 80% or more, with a nucleic acid having a base sequence of SEQ ID NO: 1:

(e) a nucleic acid having a base sequence of SEQ ID NO: 3, 5, 7, 9, 11, 13, 15 or 17;

(f) a nucleic acid encoding a protein having an amino acid sequence of SEQ ID NO: 4, 6, 8, 10, 12, 14, 16 or 18;

(g) a nucleic acid having a sequence identity of 90% or more with the nucleic acid (e);

(h) a nucleic acid which hybridizes with a complementary chain of the nucleic acid (e) under stringent conditions.

Furthermore, the present invention relates to (3) the nucleic acid according to (2), having a sequence identity of 80% or more with a nucleic acid having the base sequence of SEQ ID NO: 1.

Furthermore, the present invention relates to (4) a nucleic acid encoding a dragline protein, comprising any one of the following nucleic acids (i) to (l) and having a sequence identity of 70% or more, preferably 80% or more, with a nucleic acid having a base sequence of SEQ ID NO: 19 and:

(i) a nucleic acid having a base sequence of SEQ ID NO: 21, 23, 25, 27, 29, 31, 33 or 35;

(j) a nucleic acid encoding a protein having an amino acid sequence of SEQ ID NO: 22, 24, 26, 28, 30, 32, 34 or 36;

(k) a nucleic acid having a sequence identity of 90% or more with the nucleic acid (i);

(l) a nucleic acid which hybridizes with a complementary chain of the nucleic acid (i) under stringent conditions.

Furthermore, the present invention relates to (5) the nucleic acid according to (4), having a sequence identity of 80% or more with a nucleic acid having a base sequence of SEQ ID NO: 19.

Furthermore, the present invention relates to (6) a protein encoded by the nucleic acid according to any one of (1) to (5).

By the aforementioned specific nucleic acid according to the present invention, an MaSp protein (dragline protein) with excellent physical properties different from conventional MaSp proteins is coded and the provision of a new material of a natural fiber becomes possible. Particularly, a dragline protein encoded by the nucleic acid of the present invention (the protein according to the present invention) has more excellent elasticity (or resiliency, stretchability, degree of elongation, flexibility) than a conventional one, and preferably employed in various industrial fields, more specifically, in uses requiring elasticity such as medical products and apparel products.

Furthermore, the present invention relates to (7) a recombinant organism having the nucleic acid according to any one of (1) to (5) introduced therein and (9) a protein produced by the recombinant organism according to (7). According to the recombinant organism of the present invention, a large amount of dragline protein with excellent physical properties encoded by the nucleic acid can be produced. Proteins produced by the recombinant organism can be preferably used in various industrial fields, since they comprise a dragline protein with excellent physical properties.

In particular, the present invention relates to (8) a recombinant silkworm having the nucleic acid according to any one of (1) to (5) introduced therein and (10) a silk thread produced by the recombinant silkworm according to (8). According to the recombinant silkworm of the present invention, a large amount of silk thread comprising a dragline protein with excellent physical properties encoded by the nucleic acid can be produced. The silk thread produced by the recombinant silkworm has more excellent physical properties than conventional silk threads, and particularly has excellent elasticity, since it comprises a dragline protein with excellent physical properties.

Furthermore, the present invention relates to (11) a dragline protein having an amino acid sequence (m) or (n):

(m) an amino acid sequence of SEQ ID NO: 2 or 20;

(n) an amino acid sequence having a sequence identity of 90% or more with the amino acid sequence (m).

Furthermore, the present invention relates to (12) a dragline protein having the following amino acid sequence (o) or (p):

(o) an amino acid sequence having the following amino acid sequence (o1) or (o2) and having a sequence identity of 70% or more, preferably 80% or more, with the amino acid sequence of SEQ ID NO: 2;

(o1) an amino acid sequence of SEQ ID NO: 4, 6, 8, 10, 12, 14, 16 or 18;

(o2) an amino acid sequence having a sequence identity of 90% or more with the amino acid sequence (o1);

(p) an amino acid sequence having the following amino acid sequence (p1) or (p2) and having a sequence identity of 70% or more, preferably 80% or more, with the amino acid sequence of SEQ ID NO: 20;

(p1) an amino acid sequence of SEQ ID NO: 22, 24, 26, 28, 30, 32, 34 or 36;

(p2) an amino acid sequence having a sequence identity of 90% or more with the amino acid sequence (p1).

Furthermore, the present invention relates to (13) the dragline fiber protein according to (12), wherein the amino acid sequence (o) has a sequence identity of 80% or more with the amino acid sequence of SEQ ID NO: 2 and the amino acid sequence (p) has a sequence identity of 80% or more with the amino acid sequence of SEQ ID NO: 20.

Furthermore, the present invention relates to (14) a protein having an amino acid sequence represented by the following formula (1) or an amino acid sequence having a sequence identity of 90% or more with the amino acid sequence represented by the formula (1):

$$[X1\text{-}X2\text{-}X3\text{-}(X4)_m\text{-}(X5)_m\text{-}(X6)_m\text{-}X7\text{-}X8]_n \qquad (1).$$

In the formula (1), each m independently represent an integer of 0 or 1; n represents an integer of 1 to 10; X1 represents any one of the amino acid sequences of SEQ ID NO: 37 to 45; X2 represents any one of the amino acid sequences of SEQ ID NO: 46 to 52; X3 represents any one of the amino acid sequences of SEQ ID NO: 53 to 59; X4 represents an amino acid sequence of SEQ ID NO: 49; X5 represents an amino acid sequence of SEQ ID NO: 60 or 61; X6 represents any one of the amino acid sequences of SEQ ID NO: 62 to 64; X7 represents any one of the amino acid sequences of SEQ ID NO: 65 to 70; and X8 represents any one of the amino acid sequences of SEQ ID NO: 71 to 81.

The protein according to the present invention has more excellent physical properties due to its unique structure than conventional dragline proteins and thus preferably used in various industrial fields.

By a nucleic acid of the present invention, a protein with excellent physical properties is provided. Furthermore, by a recombinant organism of the present invention, a protein with excellent physical properties can be produced in a large amount. Particularly, by a recombinant silkworm of the present invention, a silk thread with excellent physical properties can be produced in a large amount. The dragline protein or silk thread provided by the present invention has particularly excellent elasticity. As described above, according to the present invention, it is possible to provide a new material of a natural fiber with excellent physical properties such as elasticity.

BRIEF DESCRIPTION OF THE DRAWINGS

FIG. 1 is a view showing cDNA sequence of NP-dragline protein A.

FIG. 2 is a view showing an amino acid sequence of NP-dragline protein A.

FIG. 4 is a view showing cDNA sequence of NP-dragline protein B.

FIG. 5 is a view showing an amino acid sequence of NP-dragline protein B.

DESCRIPTION OF THE PREFERRED EMBODIMENTS

Figure 3:
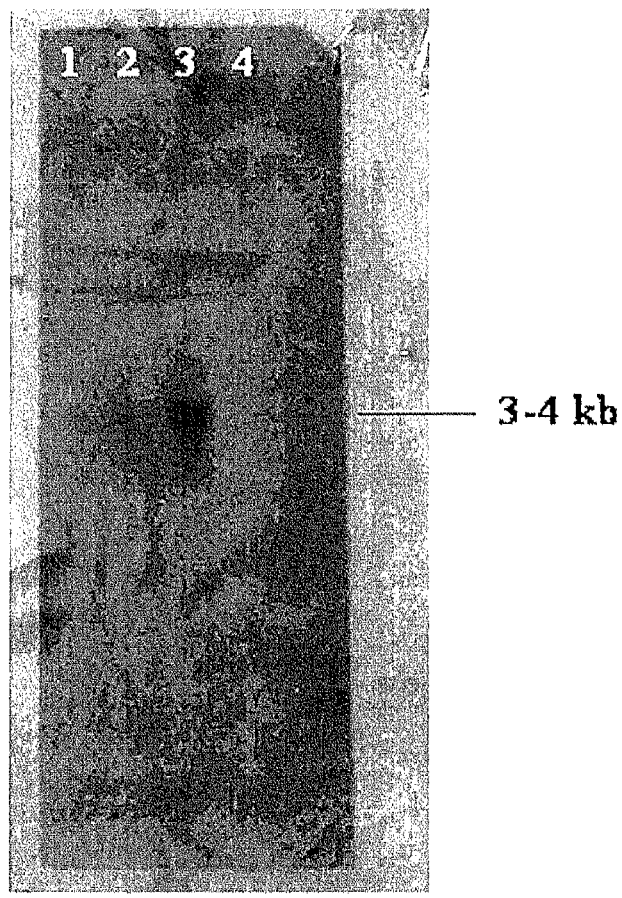
FIG. 3 is a photograph showing a result of Northern hybridization.

An embodiment for performing the invention will be described below, if necessary, referring to the accompanying drawings. However, the present invention is not limited to the following embodiment.

The present invention relates to any one of the following nucleic acids:

(a) a nucleic acid having a base sequence of SEQ ID NO: 1 or 19;

(b) a nucleic acid encoding a protein having an amino acid sequence of SEQ ID NO: 2 or 20;

(c) a nucleic acid encoding a dragline protein and having a sequence identity of 90% or more with the nucleic acid (a);

(d) a nucleic acid which encodes a dragline protein and hybridizes with a complementary chain of the nucleic acid (a) under stringent conditions.

First, the present invention relates to a nucleic acid (a) having a base sequence of SEQ ID NO: 1 or 19. Both base sequences of SEQ ID NO: 1 and 19 are genes encoding a protein (polypeptide) called Major Ampullate Spidroin (MaSp), which is a main component constituting a dragline of *Nephila pilipes* of the genus *Nephila*. In this specification, a protein encoded by a nucleic acid having the base sequence of SEQ ID NO: 1 is called "NP-dragline protein A"; a protein encoded by a nucleic acid having the base sequence of SEQ ID NO: 19 is called "NP-dragline protein B". These nucleic acids (a) are not necessarily those obtained from *Nephila pilipes* and may be artificially synthesized or obtained from a genomic library or a cDNA library or may be obtained by amplifying each of these nucleic acids by PCR and obtained by digestion with restriction enzymes, as long as a nucleic acid has an base sequence of SEQ ID NO: 1 or 19.

The nucleic acid of the present invention may be the nucleic acid (b) encoding a protein having an amino acid sequence of SEQ ID NO: 2 or 20. Both amino acid sequences of SEQ ID NO: 2 and 20 are an amino acid sequences that an MaSp protein of *Nephila pilipes* has. Specifically the amino acid sequence of SEQ ID NO: 2 is an amino acid sequence that NP-dragline protein A has, and the amino acid sequence of SEQ ID NO: 20 is an amino acid sequence that NP-dragline protein B has.

Furthermore, the nucleic acid of the present invention may be the nucleic acid (c) having a sequence identity of 90% or more with a nucleic acid having a base sequence of SEQ ID NO: 1 or 19, as long as the nucleic acid encodes a dragline protein (MaSp). The sequence identity may be 90% or more, but is preferably 93% or more, more preferably 95% or more and further preferably 98% or more.

Furthermore, the nucleic acid of the present invention may be the nucleic acid (d) which hybridizes with a complementary chain of a nucleic acid having the base sequence of SEQ ID NO: 1 or 19 under stringent conditions as long as the nucleic acid encodes a dragline protein. Herein, "complementary chain" of a nucleic acid refers to a nucleotide sequence which pairs through hydrogen bonding between nucleic acid bases (for example, T to A, C to G). Furthermore, "hybridize" means to form complementary bonding between complementary chains or form interaction between bases of single-strand nucleic acid molecules.

Herein, "stringent conditions" refers to conditions under which a complementary chain of a nucleotide chain having a homology with a target sequence preferentially hybridizes with the target sequence and a complementary chain of a nucleotide chain having no homology does not substantially hybridize. The stringent conditions are dependent upon the sequence and vary depending upon various situations. As a sequence becomes longer, specific hybridization thereof occurs at a further higher temperature. Generally, for stringent conditions, a temperature is selected so that it is about 5° C. lower than the thermal melting temperature ($T_m$) of a specific sequence at a predetermined ion strength and pH. $T_m$ is the temperature at which 50% of complementary nucleotides to a target sequence hybridize with the target sequence in an equilibrium state at a predetermined ion strength, pH and nucleic acid concentration. "Stringent conditions" are dependent upon the sequence and vary depending upon various environmental parameters. A general principle of nucleic acid hybridization can be found in Tijssen (Tijssen (1993), Laboratory Techniques In Biochemistry And Molecular Biology-Hybridization With Nucleic Acid Probes Part I, Chapter 2 "Overview of principles of hybridization and the strategy of nucleic acid probe assay", Elsevier, New York).

Typically, the stringent conditions are those in which the salt concentration is less than about 1.0 M $Na^+$, typically about 0.01 to 1.0 M of $Na^+$ concentration (or another salt) at pH 7.0 to 8.3; and the temperature is at least about 30° C. for a short nucleotide (for example, 10 to 50 nucleotides) and at least about 60° C. for a long nucleotide (for example, longer than 50 nucleotides). The stringent conditions can be also achieved by addition of an unstablizing agent such as formamide. The stringent conditions referred in this specification include hybridization in a buffer solution of 50% formamide, 1M NaCl, 1% SDS (37° C.) and washing with 0.1×SSC at 60° C.

The nucleic acid of the present invention may be a nucleic acid having a sequence identity of 70% or more with a nucleic acid having the base sequence of SEQ ID NO: 1 as long as it comprises any one of the following nucleic acids (e) to (h) and encodes a dragline protein. The sequence identity is satisfactorily 70% or more, preferably 75% or more, more preferably 80% or more, further preferably 85% or more, and particularly preferably 88% or more. The nucleic acids are:

(e) a nucleic acid having a base sequence of SEQ ID NO: 3, 5, 7, 9, 11, 13, 15 or 17;

(f) a nucleic acid encoding a protein having an amino acid sequence of SEQ ID NO: 4, 6, 8, 10, 12, 14, 16 or 18;

(g) a nucleic acid having a sequence identity of 90% or more with the nucleic acid (e);

(h) a nucleic acid which hybridizes with a complementary chain of the nucleic acid (e) under stringent conditions.

In the base sequence of SEQ ID NO: 1, base sequences of SEQ ID NO: 3, 5, 7, 9, 11, 13, 15 and 17 are a sequences which have an important characteristics for encoding a dragline protein of the present invention with excellent physical properties. By the inclusion of the nucleic acid having such a characteristic sequence, even a nucleic acid having a sequence identity of only 70% or more with a nucleic acid having the base sequence of SEQ ID NO: 1 is made capable of encoding a dragline protein of the present invention with excellent physical properties as well as the nucleic acid having the base sequence of SEQ ID NO: 1.

A protein having an amino acid sequence of SEQ ID NO: 4, 6, 8, 10, 12, 14, 16 or 18 is a protein encoded by a base sequences of SEQ ID NO: 3, 5, 7, 9, 11, 13, 15 or 17, respectively.

The sequence identity of the nucleic acid (g) with the nucleic acid (e) may be 90% or more, but is preferably 93% or more, more preferably 95% or more and further preferably 98% or more.

Furthermore, the nucleic acid of the present invention may be a nucleic acid having a sequence identity of 70% or more with a nucleic acid having the base sequence of SEQ ID NO: 19 as long as it comprises any one of the following nucleic acids (i) to (l) and encodes a dragline protein. The sequence identity may be 70% or more, but is preferably 75% or more, more preferably 80% or more, further preferably 85% or more and particularly preferably 88% or more. The nucleic acids are:

(i) a nucleic acid having a base sequence of SEQ ID NO: 21, 23, 25, 27, 29, 31, 33 or 35;

(j) a nucleic acid encoding a protein having an amino acid sequence of SEQ ID NO: 22, 24, 26, 28, 30, 32, 34 or 36;

(k) a nucleic acid having a sequence identity of 90% or more with the nucleic acid (i);

(l) a nucleic acid which hybridizes with a complementary chain of the nucleic acid (i) under stringent conditions.

In the base sequence of SEQ ID NO: 19, base sequences of SEQ ID NO: 21, 23, 25, 27, 29, 31, 33 or 35 are sequences which have an important characteristics for encoding a dragline protein of the present invention with excellent physical properties. By the inclusion of the nucleic acid having such a characteristic sequence, even a nucleic acid having a sequence identity of only 70% or more with the nucleic acid having the base sequence of SEQ ID NO: 19 can be made capable of encoding a dragline protein with excellent physical properties of the present invention as well as the nucleic acid having the base sequence of SEQ ID NO: 19.

A protein having an amino acid sequence of SEQ ID NO: 22, 24, 26, 28, 30, 32, 34 or 36 is a protein encoded by a base sequences of SEQ ID NO: 21, 23, 25, 27, 29, 31, 33 or 35, respectively.

The sequence identity of the nucleic acid (k) with the nucleic acid (i) may be 90% or more, but is preferably 93% or more, more preferably 95% or more and further preferably 98% or more.

Furthermore, the present invention relates to a recombinant organism into which a nucleic acid of the present invention as mentioned above is introduced and a protein produced by the recombinant organism. Particularly, the present invention relates to a recombinant silkworm into which a nucleic acid of the present invention as mentioned above is introduced and a silk thread produced by the recombinant silkworm.

In this specification, "recombinant organism" refers to an organism transformed by introducing a foreign gene into the chromosome by means of genetic recombination. The organism to be transformed is not particularly limited and, for example, an insect, an animal, a plant or a microorganism may be used; however, an insect is preferred. Examples of the preferable insect include *Bombyx mori, Bombyx mandarina, Antheraea yamamai* and *Antheraea pernyi*. Among them, *Bombyx mori* and *Bombyx mandarina* belonging to Bombycidae are preferably used, and *Bombyx mori* is particularly preferably used.

In this specification, "silkworm" refers to *Bombyx mori*. A silkworm may be either a breed for experimentation or a commercial breed commercialized for practical use. Furthermore, "recombinant silkworm" refers to a silkworm transformed by introducing a foreign gene into the silkworm chromosome by means of genetic recombination. Genetic recombination is performed by a method, for example, using a transposon; however, the method is not limited and any method is used as long as it can introduce a foreign gene into a silkworm and recombination of a gene can be performed by other methods including electroporation.

In this specification, "silk thread" is a fiber, which is ejected by Bombyx mori, constituting a cocoon and comprising a fibroin protein as a main component. The fibroin protein is composed of two large and small subunits (H-chain and L chain).

In this specification, "Nephila pilipes" refers to Nephila pilipes of the genus Nephila without particularly limiting their growing district.

FIG. 1 is a view showing cDNA sequence of NP-dragline protein A SEQ ID NO: 1.

FIG. 2 is a view showing an amino acid sequence of NP-dragline protein A SEQ ID NO: 2.

FIG. 3 is a photograph showing a result of Northern hybridization.

FIG. 4 is a view showing cDNA sequence of NP-dragline protein B SEQ ID NO: 19.

FIG. 5 is a view showing an amino acid sequence of NP-dragline protein B SEQ ID NO: 20.

Furthermore, the sequence identity of the amino acid sequence (o2) with the amino acid sequence (o1) is satisfactorily 90% or more, preferably 93% or more, more preferably 95% or more and further preferably 98% or more.

Similarly, the sequence identity of the amino acid sequence (p2) with the amino acid sequence (p1) is satisfactorily 90% or more, preferably 93% or more, more preferably 95% or more and further preferably 98% or more.

Furthermore, the present invention relates to a protein having an amino acid sequence represented by the following formula (1):

$$[X1-X2-X3-(X4)_m-(X5)_m-(X6)_m-X7-X8]_n \quad (1)$$

An amino acid sequence represented by the formula (1) has the "n" number of repeat units represented by [X1-X2-X3-(X4)$_m$-(X5)$_m$-(X6)$_m$-X7-X8]. The number "n" of repeat units is not particularly limited; however, the number is preferably 1 to 10, more preferably 2 to 9, further preferably 3 to 8, and particularly preferably n=8.

In the formula (1), each m independently represent an integer of 0 or 1. More specifically, there is a repeat unit having an amino acid sequence represented by X4, X5 or X6 and a repeat unit having no such an amino acid sequence.

In the formula (1), X1 represents any one of the amino acid sequences of SEQ ID NO: 37 to 45; X2 represents any one of the amino acid sequences of SEQ ID NO: 46 to 52; X3 represents any one of the amino acid sequences of SEQ ID NO: 53 to 59; X4 represents an amino acid sequence of SEQ ID NO: 49; X5 represents an amino acid sequence of SEQ ID NO: 60 or 61; X6 represents any one of the amino acid sequences of SEQ ID NO: 62 to 64; X7 represents any one of the amino acid sequences of SEQ ID NO: 65 to 70; and X8 represents any one of the amino acid sequences of SEQ ID NO: 71 to 81.

Furthermore, the protein according to the present invention may be a protein having an amino acid sequence having a sequence identity of 90% or more with an amino acid sequence represented by the formula (1). The sequence identity may be 90% or more, but is preferably 93% or more, more preferably 95% or more and further preferably 98% or more.

FIG. 1 is a view showing cDNA sequence of NP-dragline protein A, which is an MaSp protein of Nephila pilipes. The gene sequence shown in FIG. 1 is identical with the base sequence of SEQ ID NO: 1.

FIG. 2 is a view showing the amino acid sequence of NP-dragline protein A encoded by a nucleic acid having the gene sequence (base sequence of SEQ ID NO: 1) shown in FIG. 1. The amino acid sequence shown in FIG. 2 is identical with the amino acid sequence of SEQ ID NO: 2.

Furthermore, FIG. 4 is a view showing cDNA sequence of NP-dragline protein B, which is another MaSp protein of Nephila pilipes. The gene sequence shown in FIG. 4 is identical with the base sequence of SEQ ID NO: 19.

FIG. 5 is a view showing the amino acid sequence of NP-dragline protein B encoded by a nucleic acid having the gene sequence (base sequence of SEQ ID NO: 19) shown in FIG. 4. The amino acid sequence shown in FIG. 5 is identical with the amino acid sequence of SEQ ID NO: 20.

As shown in FIG. 2 or FIG. 5, the dragline protein encoded by a nucleic acid having a base sequence of SEQ ID NO: 1 or 19 is composed of the amino acid sequence represented by the following the formula (2):

$$[(\alpha)(V)(\beta)]_q \quad (2)$$

The amino acid sequence represented by the formula (2) has the "q" number of repeat units represented by [(α)(V)(β)]. The number "q" of repeat units is not particularly limited; however, the number is satisfactorily 1 to 100, preferably 1 to 10, more preferably 2 to 9, and further preferably 3 to 8, and particularly preferably q=8.

In the formula (2), (α) is composed of a glycine-rich sequence having 2 to 4 GGX units arranged next to each other and represents an amorphous region where an non-crystalline α-helix structure is formed. (V) represents a paracrystalline region rich in GX content and (β) represents a crystal region rich in alanine or threonine where a β-pleat sheet is formed.

X comprised in the (α) and (V) is more likely to represent glutamine, alanine, serine, leucine, proline, tyrosine etc., but is not limited to these and may represent a different amino acid other than those mentioned above. Furthermore, it is not necessary that a plurality of X are the same amino acids.

A specific molecular structure of the dragline protein shown in FIG. 2 or FIG. 5 and the physical properties of a dragline protein obtained by the structure will be described below.

First, in the (α) region (non-crystalline amorphous region) of the dragline protein shown in FIG. 2 or FIG. 5, 4 units of GGX are arranged next to each other. By virtue of such a sequence, a dragline forms a-helix structure. Usually, α-helix structure is bent in a fiber, but it changes into linear conformation along the fiber axis by stretching. Likewise, upon external stress α-helix structure is drastically elongated and thereby the fiber becomes elastic. On the other hand, in a conventionally known spider dragline protein (MaSp), 4 units of GGX arranged next to each other can not be found (see Non-Patent Literature 1, 2 etc.). From the above, since a unique structure having 4 units of GGX arranged next to each other is formed in the (α) region, the elasticity (or resiliency, stretchability, degree of elongation, flexibility) of the dragline protein obtained by the present invention conceivably improves.

A finding that a thread becomes elastic by the presence of a GGX repeat motif is descried in the following documents:

Cheryl Y. Hayashi et al., Evidence from Flagelliform Silk cDNA for the Structural Basis of Elasticity and Modular Nature of Spider Silks, 1998, p. 779;

Thomas Scheibel, Spider silks: recombinant synthesis, assembly, spinning, and engineering of synthetic proteins, 2004, p. 2.

Furthermore, the (V) region (paracrystalline region) of the dragline protein shown in FIG. 2 or FIG. 5 is rich in a hydrophilic amino acid. As shown in Table 1, the dragline protein shown in FIG. 2 or FIG. 5 is rich in a hydrophilic amino acid compared to a dragline protein of conventionally known *Nephila clavipes* (North America) and Japanese *Nephila clavata*. By virtue of this, it is considered that a dragline protein obtained by the present invention increases in hygroscopicity. Furthermore, low crystallinity of a dragline protein is conceivably a factor of increasing hygroscopicity.

Furthermore, in the (β) region (crystalline region) of the dragline protein shown in FIG. 2 or FIG. 5, polar amino acids such as threonine and asparagine are comprised between polyalanines. Since the dragline protein obtained by the present invention has a polyalanine (Poly(A)) motif rich in polar amino acid, excellent toughness is conceivably obtained.

The finding that a thread becomes tough by the presence of a polyalanine (Poly(A)) motif rich in polar amino acid is described in the following documents:

Glareh Askarieh et al., Self-assembly of spider silk proteins is controlled by a pH-sensitive relay, 2010, vol. 465, p. 1;

J. M. GOSLINE, et al., THE MECHANICAL DESIGN OF SPIDER SILKS: FROM FIBROIN SEQUENCE TO MECHANICAL FUNCTION, 1999, p. 3299.

Furthermore, as shown in Table 1, the dragline protein shown in FIG. 2 or FIG. 5 comprises a polar amino acid twice as large as in conventionally known *Nephila clavipes* (North America) and Japanese *Nephila clavata*. By the presence of the polar amino acid residue present in a large amount within a molecule as mentioned, when external stress is applied, molecules are regularly arranged along the direction of the applied stress to increase interaction force between the molecules. In this manner, the dragline acquires excellent strength. In particular, hydrogen bonding between molecules conceivably plays a role in increasing the strength of a thread fiber.

Table 1 shows the contents of a polar amino acid and a hydrophilic amino acid in MaSp protein of *Nephila pilipes*, *Nephila clavipes* (North America), Japanese *Nephila clavata*. The content of a polar amino acid represents the content of N (Asn), C (Cys), Q (Gln), S (Ser), T (Thr) and Y (Tyr) and the content of a hydrophilic amino acid represents the contents of R (Arg), N (Asn), D (Asp), Q (Gln), E (Glu), H (His), K (Lys), S (Ser) and T (Thr).

TABLE 1

|  | Polar amino acid (%) | Hydrophilic amino acid (%) |
| --- | --- | --- |
| *Nephila pilipes* | 31.05 | 29.41 |
| *Nephila clavipes* (North America) | 15.71 | 14.85 |
| Japanese *Nephila clavata* | 15.15 | 11.01 |

EXAMPLES

The present invention will be more specifically described by way of Examples. However, the present invention is not limited to the following Examples.

As a test animal, a female adult spider of *Nephila pilipes* collected in July was used.

(RNA Extraction)

Total RNA was prepared from the Major Ampullate of the spider of *Nephila pilipes*. The Major Ampullate of the spider was dissected in physiological saline solution (NaCl 0.75%) and TRIZOL (1 ml) was added thereto and sufficiently ground. The resultant suspension solution was separated with chloroform (200 μl) and removed. The water layer was transferred to another tube and the same amount of isopropanol was added thereto to precipitate RNA. The precipitate was rinsed with 75% ethanol and stored at −80° C. Thereafter, it was centrifuged at 7500 rpm, 4° C. for 5 minutes, dried for 8 minutes in vacuum, and dissolved in RNase-free water at 55° C. for 10 minutes and used as a sample. The sample was subjected to agarose electrophoresis to confirm extraction of RNA.

(Construction of cDNA Library)

Synthesis and construction of cDNA library of the Major Ampullate by the G-capping method was outsourced to Takara Bio Inc. A library vector (pDNR-LIB) was dissolved in TE (about 50 μl).

(Cloning and Sequence)

An electroporation method was employed to perform transformation at a high probability. The cDNA library solution prepared was used as a DNA solution. As competent cells, "Electro MAX™ DH12S™ Cells" (Cat. No. 18312-017) manufactured by Invitrogen were used. As a cuvette, a cuvette of 0.1 cm in size was used.

First, a cuvette was cooled on ice in advance. After 50 μl of competent cells (>$10^{10}$ cfu/μg) in a tube were thawed on ice and 1 μl of the cDNA library solution was added to the tube. The resultant mixture solution was transferred to the cuvette so as to obtain a homogenous state. Conditions of electroporation include a voltage of 2.5 kV, a pulse controller ($R_{2-7}$) 200Ω, a capacitance of 25 μF. Pulse was applied once and 1 ml of SOC medium (2% Bacto tryptone, 0.5% Bacto yeast extract, 10 mM NaCl, 2.5 mM KCl, 10 mM $MgCl_2$, 10 mM $MgSO_4$, 20 mM glucose) was added to the cuvette as soon as possible to suspend the solution. The suspension solution was transferred to a culture tube and cultured for 1 to 1.5 hours, and thereafter scattered on an LB plate (1% Bacto tryptone, 0.5% Bacto yeast extract, 0.5% NaCl) comprising an antibiotic substance (ampicillin), IPTG and X-Gal. White colony grown in the plate was taken and inoculated on LB (+ampicillin) medium, 588 recombinant plasmids were selected at random and purified by use of FlexiPrep™ Kit (manufactured by Amersham plc).

(Sequence and Comparative Analysis of Sequence)

The sequence of an insert was analyzed by "ABI Prism genetic analyzer 3100" (manufactured by Life Technologies Corporation) and T7 primer. Computer analysis of DNA and an amino acid sequence was performed by use of "Genetyx package" (manufactured by Genetyx Corporation) and "Sequencher 4.14" (Demo version) (manufactured by Gene Codes Corporation). Sequence comparison was made based on homology analysis of protein data base by means of SIB BLAST Network Service of an ExPASy Proteomics server (http://www.expasy.org).

(Experiment for Proving Specific Expression of Silk Gland) MaSp (major ampullate spidroin) is expressed in the major ampullate as the name implies. To prove that the gene of the present invention works in the major ampullate, a Northern hybridization experiment was performed between a probe, which was prepared by using the 3' end sequence of a cDNA sequence (the C terminal of the amino acid sequence) and RNA samples extracted from 4 silk glands of a spider (flagelliform gland, tubular gland, major ampullate, minor ampullate). FIG. 3 shows the results of the Northern hybridization. To lanes 1 to 4 of FIG. 3, RNA samples extracted from flagelliform gland, tubular gland, major ampullate and minor ampullate were supplied and flow respectively in this order. From the results, it was found that the gene (nucleic acid) of the present invention is specifically expressed in the major ampullate of *Nephila pilipes*. Furthermore, the molecular weight of the transcribed substance was estimated to be about 3 to 4 kb.

(Evaluation on Physical Properties of Dragline)

To compare the dragline of *Nephila pilipes* and the dragline of a conventionally known spider in physical properties, the degree of elongation (elastic modulus) of each of the fibers was measured. At the day before measurement, sample draglines were allowed to stand still at 20° C., RH65% for 24 hours to adjust the moisture contents thereof. Then, the sample fibers of 20 mm were subjected to an elongation test performed under the conditions: 20° C., RH65% at a stretch rate of 20 mm/min by using a tension tester, "Tensilon UTM-III-100" (manufactured by Toyo Baldwin). As a conventionally known spider, Japanese *Nephila clavata* and *Argiope bruennichi* were used. The results are shown in Table 2.

TABLE 2

|  | Elongation (%) |
| --- | --- |
| *Argiope bruennichi* | 26.1 |
| Japanese *Nephila clavata* | 22.3 |
| *Nephila pilipes* | 29.4 |

As shown in Table 2, it was found that the dragline of *Nephila pilipes* has excellent elasticity compared to those of conventionally known spiders. More specifically, it was demonstrated that the nucleic acid of the present invention encodes a dragline protein with excellent elasticity.

The dragline protein provided by the present invention, since it is natural fiber excellent in elasticity, can be preferably used as a new material in various industrial fields such as medical, aviation and apparel industries.

What is claimed is:

1. An isolated protein encoded by one of the following nucleic acids (i)-(iv):
   (i) a nucleic acid having the base sequence of SEQ ID NO: 1;
   (ii) a nucleic acid encoding a protein having the amino acid sequence of SEQ ID NO: 2:
   (iii) a nucleic acid encoding a dragline protein with a base sequence identity of 90% or more to SEQ ID NO: 1; or
   (iv) a nucleic acid which encodes a dragline protein and hybridizes with the complementary chain of the nucleic acid of SEQ ID NO: 1 under stringent conditions including hybridization in a buffer solution of 50% formamide, 1M NaCl, 1% SDS at 37° C. and washing with 0.1×SSC at 60° C.

2. An isolated protein produced by a recombinant silkworm having a nucleic acid introduced therein, wherein the nucleic acid is one of the following nucleic acids (i)-(iv):
   (i) a nucleic acid having the base sequence of SEQ ID NO: 1;
   (ii) a nucleic acid encoding a protein having the amino acid sequence of SEQ ID NO: 2:
   (iii) a nucleic acid encoding a dragline protein with a base sequence identity of 90% or more to SEQ ID NO: 1; or
   (iv) a nucleic acid which encodes a dragline protein and hybridizes with the complementary chain of the nucleic acid of SEQ ID NO: 1 under stringent conditions including hybridization in a buffer solution of 50% formamide, 1M NaCl, 1% SDS at 37° C. and washing with 0.1×SSC at 60° C.

3. An isolated silk thread produced by a recombinant silkworm having a nucleic acid introduced therein, wherein the nucleic acid is one of the following nucleic acids (i)-(iv):
   (i) a nucleic acid having the base sequence of SEQ ID NO: 1;
   (ii) a nucleic acid encoding a protein having the amino acid sequence of SEQ ID NO: 2;
   (iii) a nucleic acid encoding a dragline protein with a base sequence identity of 90% or more to SEQ ID NO: 1; or
   (iv) a nucleic acid which encodes a dragline protein and hybridizes with the complementary chain of the nucleic acid of SEQ ID NO: 1 under stringent conditions including hybridization in a buffer solution of 50% formamide, 1M NaCl, 1% SDS at 37° C. and washing with 0.1×SSC at 60° C.

4. An isolated dragline protein having an amino acid sequence selected from the group consisting of:
   (i) the amino acid sequence of SEQ ID NO: 2; and
   (ii) an amino acid sequence having a sequence identity of 90% or more with SEQ ID NO: 2.

5. An isolated dragline protein having the following amino acid sequence:
   an amino acid sequence comprising a sequence selected from the group consisting of SEQ ID NO: 4, 6, 8, 10, 12, 14, 16 and 18 and further having an overall sequence identity of 80% or more with the amino acid sequence of SEQ ID NO: 2.

* * * * *

SEQUENCE LISTING

```
<160> NUMBER OF SEQ ID NOS: 81

<210> SEQ ID NO 1
<211> LENGTH: 1000
<212> TYPE: DNA
<213> ORGANISM: Nephila pilipes

<400> SEQUENCE: 1
gggggatatg gagcaggaag tggatctacc atcgcaataa ctgctggtgg tcttggtgga      60
tctggaggtc aaggtggcca aataccatct ggcgctgttg gacaaggaac tcaaggatat     120
ggaacaggaa gtggagcaac catcgcatta actgctggtg gacttggggg acaaggtggt     180
caaggaccat ctggctctgg tggacaaggc ccatcaggac aaggagctca aggacctggc     240
ggatatggag caggaaatgc agccgccgcc aacgcagcag ctagtggact tggaggctat     300
ggagttggtg ggcagggaag tggccaaaga ccatctggag ctggtggaca aggtgctcaa     360
gcgccaggtg gatatggaac aggaagtgga tcgaccatcg taataactgc tggtggacag     420
agaggacaag gtggtcaagg accatcagga caattagctc aagcacctag tggatatgga     480
caaggaagtg gagccgccgc cgcctctggt ggtcttggag gatatggagg tcaaggtggc     540
caaagatcat ctggcgctgg tgcacaagga actcaaggat atggtacagg aagtggaaca     600
actatcgcat taactgctgg tggtattgga ggatctggag gtcaaggtgg ccaaagacca     660
tctggcattg gtggacaagg agctcaaggg ccaggtggat atggagcagg aagtggatct     720
accatcgcaa taactactgg tggtcttggt ggatatggag gtcaaggtgg ccaaagacca     780
tctggcgctg atggacaagg agctcaagga tatggaacag gaagtggagc taccatcgct     840
ttaactgctg gtggacttgg aggttatggt ggacagagag gtcaagttgg tcaaggacca     900
tcaggacaat tagctggagc acctggtgga tatggacaag gaagtgcagc cgccacggca     960
gctggtggac ttcgaggttt cgggcaaggg ttacaagtac                          1000

<210> SEQ ID NO 2
<211> LENGTH: 306
<212> TYPE: PRT
<213> ORGANISM: Nephila pilipes

<400> SEQUENCE: 2
```

```
Gly Gly Leu Gly Gly Ser Gly Gln Gly Gln Ile Pro Ser Gly
  1               5                  10                  15

Ala Val Gly Gln Gly Thr Gln Gly Tyr Gly Thr Gly Ser Gly Ala Thr
             20                  25                  30

Ile Ala Leu Thr Ala Gly Gly Leu Gly Gly Gln Gly Gly Gln Gly Pro
         35                  40                  45

Ser Gly Ser Gly Gly Gln Gly Pro Ser Gly Gln Gly Ala Gln Gly Pro
 50                  55                  60

Gly Gly Tyr Gly Ala Gly Asn Ala Ala Ala Asn Ala Ala Ala Ser
 65                  70                  75                  80

Gly Leu Gly Gly Tyr Gly Val Gly Gly Gln Gly Ser Gly Gln Arg Pro
                 85                  90                  95

Ser Gly Ala Gly Gly Gln Gly Ala Gln Ala Pro Gly Gly Tyr Gly Thr
             100                 105                 110

Gly Ser Gly Ser Thr Ile Val Ile Thr Ala Gly Gly Gln Arg Gly Gln
             115                 120                 125

Gly Gly Gln Gly Pro Ser Gly Gln Leu Ala Gln Ala Pro Ser Gly Tyr
         130                 135                 140

Gly Gln Gly Ser Gly Ala Ala Ala Ala Ser Gly Gly Leu Gly Gly Tyr
145                 150                 155                 160

Gly Gly Gln Gly Gly Gln Arg Ser Ser Gly Ala Gly Ala Gln Gly Thr
                 165                 170                 175

Gln Gly Tyr Gly Thr Gly Ser Gly Thr Thr Ile Ala Leu Thr Ala Gly
             180                 185                 190

Gly Ile Gly Gly Ser Gly Gly Gln Gly Gly Gln Arg Pro Ser Gly Ile
         195                 200                 205

Gly Gly Gln Gly Ala Gln Gly Pro Gly Gly Tyr Gly Ala Gly Ser Gly
 210                 215                 220

Ser Thr Ile Ala Ile Thr Thr Gly Gly Leu Gly Gly Tyr Gly Gly Gln
225                 230                 235                 240

Gly Gly Gln Arg Pro Ser Gly Ala Asp Gly Gly Ala Gln Gly Tyr
                 245                 250                 255

Gly Thr Gly Ser Gly Ala Thr Ile Ala Leu Thr Ala Gly Gly Leu Gly
             260                 265                 270

Gly Tyr Gly Gly Gln Arg Gly Gln Val Gly Gln Gly Pro Ser Gly Gln
             275                 280                 285

Leu Ala Gly Ala Pro Gly Gly Tyr Gly Gln Gly Ser Ala Ala Ala Thr
 290                 295                 300

Ala Ala
305
```

<210> SEQ ID NO 3
<211> LENGTH: 111
<212> TYPE: DNA
<213> ORGANISM: Nephila pilipes

<400> SEQUENCE: 3
ggtggtcttg gtggatctgg aggtcaaggt ggccaaatac catctggcgc tgttggacaa      60
ggaactcaag gatatggaac aggaagtgga gcaaccatcg cattaactgc t             111

<210> SEQ ID NO 4
<211> LENGTH: 37
<212> TYPE: PRT
<213> ORGANISM: Nephila pilipes

```
<400> SEQUENCE: 4

Gly Gly Leu Gly Gly Ser Gly Gly Gln Gly Gly Gln Ile Pro Ser Gly
1               5                   10                  15

Ala Val Gly Gln Gly Thr Gln Gly Tyr Gly Thr Gly Ser Gly Ala Thr
            20                  25                  30

Ile Ala Leu Thr Ala
        35

<210> SEQ ID NO 5
<211> LENGTH: 126
<212> TYPE: DNA
<213> ORGANISM: Nephila pilipes

<400> SEQUENCE: 5
ggtggacttg ggggacaagg tggtcaagga ccatctggct ctggtggaca aggcccatca     60
ggacaaggag ctcaaggacc tggcggatat ggagcaggaa atgcagccgc cgccaacgca    120
gcagct                                                               126

<210> SEQ ID NO 6
<211> LENGTH: 42
<212> TYPE: PRT
<213> ORGANISM: Nephila pilipes

<400> SEQUENCE: 6

Gly Gly Leu Gly Gly Gln Gly Gly Gln Gly Pro Ser Gly Ser Gly Gly
1               5                   10                  15

Gln Gly Pro Ser Gly Gln Gly Ala Gln Gly Pro Gly Gly Tyr Gly Ala
            20                  25                  30

Gly Asn Ala Ala Ala Asn Ala Ala Ala
        35                  40

<210> SEQ ID NO 7
<211> LENGTH: 129
<212> TYPE: DNA
<213> ORGANISM: Nephila pilipes

<400> SEQUENCE: 7
agtggacttg gaggctatgg agttggtggg cagggaagtg gccaaagacc atctggagct     60
ggtggacaag gtgctcaagc gccaggtgga tatggaacag gaagtggatc gaccatcgta    120
ataactgct                                                            129

<210> SEQ ID NO 8
<211> LENGTH: 43
<212> TYPE: PRT
<213> ORGANISM: Nephila pilipes

<400> SEQUENCE: 8

Ser Gly Leu Gly Gly Tyr Gly Val Gly Gly Gln Gly Ser Gly Gln Arg
1               5                   10                  15

Pro Ser Gly Ala Gly Gly Gln Gly Ala Gln Ala Pro Gly Gly Tyr Gly
            20                  25                  30

Thr Gly Ser Gly Ser Thr Ile Val Ile Thr Ala
        35                  40

<210> SEQ ID NO 9
<211> LENGTH: 96
<212> TYPE: DNA
<213> ORGANISM: Nephila pilipes
```

```
<400> SEQUENCE: 9
ggtggacaga gaggacaagg tggtcaagga ccatcaggac aattagctca agcacctagt      60
ggatatggac aaggaagtgg agccgccgcc gcctct                               96

<210> SEQ ID NO 10
<211> LENGTH: 32
<212> TYPE: PRT
<213> ORGANISM: Nephila pilipes

<400> SEQUENCE: 10
```

Gly Gly Gln Arg Gly Gln Gly Gly Gln Gly Pro Ser Gly Gln Leu Ala
1               5                   10                  15

Gln Ala Pro Ser Gly Tyr Gly Gln Gly Ser Gly Ala Ala Ala Ala Ser
                20                  25                  30

```
<210> SEQ ID NO 11
<211> LENGTH: 111
<212> TYPE: DNA
<213> ORGANISM: Nephila pilipes

<400> SEQUENCE: 11
ggtggtcttg gaggatatgg aggtcaaggt ggccaaagat catctggcgc tggtgcacaa      60
ggaactcaag gatatggtac aggaagtgga acaactatcg cattaactgc t              111

<210> SEQ ID NO 12
<211> LENGTH: 37
<212> TYPE: PRT
<213> ORGANISM: Nephila pilipes

<400> SEQUENCE: 12
```

Gly Gly Leu Gly Gly Tyr Gly Gly Gln Gly Gly Gln Arg Ser Ser Gly
1               5                   10                  15

Ala Gly Ala Gln Gly Thr Gln Gly Tyr Gly Thr Gly Ser Gly Thr Thr
                20                  25                  30

Ile Ala Leu Thr Ala
        35

```
<210> SEQ ID NO 13
<211> LENGTH: 120
<212> TYPE: DNA
<213> ORGANISM: Nephila pilipes

<400> SEQUENCE: 13
ggtggtattg gaggatctgg aggtcaaggt ggccaaagac catctggcat tggtggacaa      60
ggagctcaag ggccaggtgg atatggagca ggaagtggat ctaccatcgc aataactact     120

<210> SEQ ID NO 14
<211> LENGTH: 40
<212> TYPE: PRT
<213> ORGANISM: Nephila pilipes

<400> SEQUENCE: 14
```

Gly Gly Ile Gly Gly Ser Gly Gly Gln Gly Gly Gln Arg Pro Ser Gly
1               5                   10                  15

Ile Gly Gly Gln Gly Ala Gln Gly Pro Gly Gly Tyr Gly Ala Gly Ser
                20                  25                  30

Gly Ser Thr Ile Ala Ile Thr Thr
        35                  40

```
<210> SEQ ID NO 15
```

```
<211> LENGTH: 111
<212> TYPE: DNA
<213> ORGANISM: Nephila pilipes

<400> SEQUENCE: 15
ggtggtcttg gtggatatgg aggtcaaggt ggccaaagac catctggcgc tgatggacaa      60
ggagctcaag gatatggaac aggaagtgga gctaccatcg ctttaactgc t              111

<210> SEQ ID NO 16
<211> LENGTH: 37
<212> TYPE: PRT
<213> ORGANISM: Nephila pilipes

<400> SEQUENCE: 16

Gly Gly Leu Gly Gly Tyr Gly Gly Gln Gly Gly Gln Arg Pro Ser Gly
1               5                   10                  15

Ala Asp Gly Gln Gly Ala Gln Gly Tyr Gly Thr Gly Ser Gly Ala Thr
            20                  25                  30

Ile Ala Leu Thr Ala
        35

<210> SEQ ID NO 17
<211> LENGTH: 114
<212> TYPE: DNA
<213> ORGANISM: Nephila pilipes

<400> SEQUENCE: 17
ggtggacttg gaggttatgg tggacagaga ggtcaagttg gtcaaggacc atcaggacaa      60
ttagctggag cacctggtgg atatggacaa ggaagtgcag ccgccacggc agct           114

<210> SEQ ID NO 18
<211> LENGTH: 38
<212> TYPE: PRT
<213> ORGANISM: Nephila pilipes

<400> SEQUENCE: 18

Gly Gly Leu Gly Gly Tyr Gly Gly Gln Arg Gly Gln Val Gly Gln Gly
1               5                   10                  15

Pro Ser Gly Gln Leu Ala Gly Ala Pro Gly Gly Tyr Gly Gln Gly Ser
            20                  25                  30

Ala Ala Ala Thr Ala Ala
        35

<210> SEQ ID NO 19
<211> LENGTH: 900
<212> TYPE: DNA
<213> ORGANISM: Nephila pilipes

<400> SEQUENCE: 19
ggtggtcttg gtggatatgg aggtcaaggt ggccaaagac tatctggcgc tagtggacaa      60
ggaactcaag gatatggaac aggaagtgga gctaccatcg ctttaactgc tggtggtcaa     120
ggtggatctg gaggtcaagg tggccaaaga ctatctggcg ctagtggaca aggaactcaa     180
ggatatggaa caggaagtgg agcaaccatc gcattaactg ctggtggact ggggggacaa     240
ggtggtcaag gaccatctgg ctctggtgga caaggcccat caggacaagg agctcaaggg     300
ccaggtggat atggaacagg aagtggaacg gccatcgcaa taactgctgg tggacagaga     360
ggacaaggtg gtcaaggacc atcaggacaa ttagctcaag cacctagtgg atatggacta     420
ggaagtggag ccgccgccgc ctttggtggt cttggaggat atgaggtcaa ggtggccaa      480
```

```
agatcatctg gcgctggtgc acaaggaact caaggatatg aacaggaag tggaacaact    540 atcgcattaa ctgctggtgg tattggagga tctggaggtc aaggtggcca aagaccatct    600
ggcgctggtg gacaaggagc tcaagggcca ggtggatatg gagcaggaag tggatctacc    660
atcgcaataa cagctggtgg tcttggtgga tctggaggtc aaggtggcca aagaccatct    720
ggcgctggtg gacaaggagc tcaaggatat ggaacaggaa gtggagctac catcgcaata    780
actgctggtg gacttggagg ttatggtgga cagagaggtc aagttggtca aggaccatca    840
ggacaattag ctggagcacc tggtggatat ggacaaggaa gtgcagccgc cacggcagct    900
```

<210> SEQ ID NO 20
<211> LENGTH: 300
<212> TYPE: PRT
<213> ORGANISM: Nephila pilipes

<400> SEQUENCE: 20

```
Gly Gly Leu Gly Gly Tyr Gly Gly Gln Gly Gly Gln Arg Leu Ser Gly
  1               5                  10                  15

Ala Ser Gly Gln Gly Thr Gln Gly Tyr Gly Thr Gly Ser Gly Ala Thr
             20                  25                  30

Ile Ala Leu Thr Ala Gly Gly Gln Gly Gly Ser Gly Gly Gln Gly Gly
         35                  40                  45

Gln Arg Leu Ser Gly Ala Ser Gly Gln Gly Thr Gln Gly Tyr Gly Thr
     50                  55                  60

Gly Ser Gly Ala Thr Ile Ala Leu Thr Ala Gly Gly Leu Gly Gly Gln
 65                  70                  75                  80

Gly Gly Gln Gly Pro Ser Gly Ser Gly Gln Gly Pro Ser Gly Gln
             85                  90                  95

Gly Ala Gln Gly Pro Gly Gly Tyr Gly Thr Gly Ser Gly Thr Ala Ile
            100                 105                 110

Ala Ile Thr Ala Gly Gly Gln Arg Gly Gln Gly Gly Gln Gly Pro Ser
        115                 120                 125

Gly Gln Leu Ala Gln Ala Pro Ser Gly Tyr Gly Leu Gly Ser Gly Ala
    130                 135                 140

Ala Ala Ala Phe Gly Gly Leu Gly Gly Tyr Gly Gly Gln Gly Gly Gln
145                 150                 155                 160

Arg Ser Ser Gly Ala Gly Ala Gln Gly Thr Gln Gly Tyr Gly Thr Gly
                165                 170                 175

Ser Gly Thr Thr Ile Ala Leu Thr Ala Gly Gly Ile Gly Gly Ser Gly
            180                 185                 190

Gly Gln Gly Gly Gln Arg Pro Ser Gly Ala Gly Gly Gln Gly Ala Gln
        195                 200                 205

Gly Pro Gly Gly Tyr Gly Ala Gly Ser Gly Ser Thr Ile Ala Ile Thr
    210                 215                 220

Ala Gly Gly Leu Gly Gly Ser Gly Gly Gln Gly Gly Gln Arg Pro Ser
225                 230                 235                 240

Gly Ala Gly Gly Gln Gly Ala Gln Gly Tyr Gly Thr Gly Ser Gly Ala
                245                 250                 255

Thr Ile Ala Ile Thr Ala Gly Gly Leu Gly Gly Tyr Gly Gly Gln Arg
            260                 265                 270

Gly Gln Val Gly Gln Gly Pro Ser Gly Gln Leu Ala Gly Ala Pro Gly
        275                 280                 285

Gly Tyr Gly Gln Gly Ser Ala Ala Ala Thr Ala Ala
    290                 295                 300
```

```
<210> SEQ ID NO 21
<211> LENGTH: 111
<212> TYPE: DNA
<213> ORGANISM: Nephila pilipes

<400> SEQUENCE: 21
ggtggtcttg tggatatgg aggtcaaggt ggccaaagac tatctggcgc tagtggacaa      60
ggaactcaag gatatggaac aggaagtgga gctaccatcg ctttaactgc t             111

<210> SEQ ID NO 22
<211> LENGTH: 37
<212> TYPE: PRT
<213> ORGANISM: Nephila pilipes

<400> SEQUENCE: 22

Gly Gly Leu Gly Gly Tyr Gly Gly Gln Gly Gly Gln Arg Leu Ser Gly
1               5                   10                  15

Ala Ser Gly Gln Gly Thr Gln Gly Tyr Gly Thr Gly Ser Gly Ala Thr
            20                  25                  30

Ile Ala Leu Thr Ala
        35

<210> SEQ ID NO 23
<211> LENGTH: 111
<212> TYPE: DNA
<213> ORGANISM: Nephila pilipes

<400> SEQUENCE: 23
ggtggtcaag gtggatctgg aggtcaaggt ggccaaagac tatctggcgc tagtggacaa      60
ggaactcaag gatatggaac aggaagtgga gcaaccatcg cattaactgc t             111

<210> SEQ ID NO 24
<211> LENGTH: 37
<212> TYPE: PRT
<213> ORGANISM: Nephila pilipes

<400> SEQUENCE: 24

Gly Gly Gln Gly Gly Ser Gly Gly Gln Gly Gly Gln Arg Leu Ser Gly
1               5                   10                  15

Ala Ser Gly Gln Gly Thr Gln Gly Tyr Gly Thr Gly Ser Gly Ala Thr
            20                  25                  30

Ile Ala Leu Thr Ala
        35

<210> SEQ ID NO 25
<211> LENGTH: 126
<212> TYPE: DNA
<213> ORGANISM: Nephila pilipes

<400> SEQUENCE: 25
ggtggacttg ggggacaagg tggtcaagga ccatctggct ctggtggaca aggcccatca      60
ggacaaggag ctcaagggcc aggtggatat ggaacaggaa gtggaacggc catcgcaata    120
actgct                                                              126

<210> SEQ ID NO 26
<211> LENGTH: 42
<212> TYPE: PRT
<213> ORGANISM: Nephila pilipes

<400> SEQUENCE: 26
```

Gly Gly Leu Gly Gly Gln Gly Gln Gly Pro Ser Gly Ser Gly Gly
1               5                   10                  15

Gln Gly Pro Ser Gly Gln Gly Ala Gln Gly Pro Gly Tyr Gly Thr
            20                  25                  30

Gly Ser Gly Thr Ala Ile Ala Ile Thr Ala
        35                  40

<210> SEQ ID NO 27
<211> LENGTH: 96
<212> TYPE: DNA
<213> ORGANISM: Nephila pilipes

<400> SEQUENCE: 27
ggtggacaga gaggacaagg tggtcaagga ccatcaggac aattagctca agcacctagt    60
ggatatggac taggaagtgg agccgccgcc gccttt                             96

<210> SEQ ID NO 28
<211> LENGTH: 32
<212> TYPE: PRT
<213> ORGANISM: Nephila pilipes

<400> SEQUENCE: 28

Gly Gly Gln Arg Gly Gln Gly Gly Gln Gly Pro Ser Gly Gln Leu Ala
1               5                   10                  15

Gln Ala Pro Ser Gly Tyr Gly Leu Gly Ser Gly Ala Ala Ala Ala Phe
            20                  25                  30

<210> SEQ ID NO 29
<211> LENGTH: 111
<212> TYPE: DNA
<213> ORGANISM: Nephila pilipes

<400> SEQUENCE: 29
ggtggtcttg gaggatatgg aggtcaaggt ggccaaagat catctggcgc tggtgcacaa    60
ggaactcaag gatatggaac aggaagtgga acaactatcg cattaactgc t            111

<210> SEQ ID NO 30
<211> LENGTH: 37
<212> TYPE: PRT
<213> ORGANISM: Nephila pilipes

<400> SEQUENCE: 30

Gly Gly Leu Gly Gly Tyr Gly Gly Gln Gly Gly Gln Arg Ser Ser Gly
1               5                   10                  15

Ala Gly Ala Gln Gly Thr Gln Gly Tyr Gly Thr Gly Ser Gly Thr Thr
            20                  25                  30

Ile Ala Leu Thr Ala
        35

<210> SEQ ID NO 31
<211> LENGTH: 120
<212> TYPE: DNA
<213> ORGANISM: Nephila pilipes

<400> SEQUENCE: 31
ggtggtattg gaggatctgg aggtcaaggt ggccaaagac catctggcgc tggtggacaa    60
ggagctcaag ggccaggtgg atatggagca ggaagtggat ctaccatcgc aataacagct   120

<210> SEQ ID NO 32
<211> LENGTH: 40
<212> TYPE: PRT

<213> ORGANISM: Nephila pilipes

<400> SEQUENCE: 32

Gly Gly Ile Gly Gly Ser Gly Gly Gln Gly Gly Gln Arg Pro Ser Gly
1               5                   10                  15

Ala Gly Gly Gln Gly Ala Gln Gly Pro Gly Gly Tyr Gly Ala Gly Ser
            20                  25                  30

Gly Ser Thr Ile Ala Ile Thr Ala
        35                  40

<210> SEQ ID NO 33
<211> LENGTH: 111
<212> TYPE: DNA
<213> ORGANISM: Nephila pilipes

<400> SEQUENCE: 33
ggtggtcttg gtggatctgg aggtcaaggt ggccaaagac catctggcgc tggtggacaa    60
ggagctcaag atatggaac aggaagtgga gctaccatcg caataactgc t             111

<210> SEQ ID NO 34
<211> LENGTH: 37
<212> TYPE: PRT
<213> ORGANISM: Nephila pilipes

<400> SEQUENCE: 34

Gly Gly Leu Gly Gly Ser Gly Gly Gln Gly Gly Gln Arg Pro Ser Gly
1               5                   10                  15

Ala Gly Gly Gln Gly Ala Gln Gly Tyr Gly Thr Gly Ser Gly Ala Thr
            20                  25                  30

Ile Ala Ile Thr Ala
        35

<210> SEQ ID NO 35
<211> LENGTH: 114
<212> TYPE: DNA
<213> ORGANISM: Nephila pilipes

<400> SEQUENCE: 35
ggtggacttg gaggttatgg tggacagaga ggtcaagttg gtcaaggacc atcaggacaa    60
ttagctggag cacctggtgg atatggacaa ggaagtgcag ccgccacggc agct          114

<210> SEQ ID NO 36
<211> LENGTH: 38
<212> TYPE: PRT
<213> ORGANISM: Nephila pilipes

<400> SEQUENCE: 36

Gly Gly Leu Gly Gly Tyr Gly Gly Gln Arg Gly Gln Val Gly Gln Gly
1               5                   10                  15

Pro Ser Gly Gln Leu Ala Gly Ala Pro Gly Gly Tyr Gly Gln Gly Ser
            20                  25                  30

Ala Ala Ala Thr Ala Ala
        35

<210> SEQ ID NO 37
<211> LENGTH: 12
<212> TYPE: PRT
<213> ORGANISM: Nephila pilipes

<400> SEQUENCE: 37

```
Gly Gly Leu Gly Gly Ser Gly Gln Gly Gln
1               5                   10

<210> SEQ ID NO 38
<211> LENGTH: 9
<212> TYPE: PRT
<213> ORGANISM: Nephila pilipes

<400> SEQUENCE: 38

Gly Gly Leu Gly Gly Gln Gly Gly Gln
1               5

<210> SEQ ID NO 39
<211> LENGTH: 15
<212> TYPE: PRT
<213> ORGANISM: Nephila pilipes

<400> SEQUENCE: 39

Ser Gly Leu Gly Gly Tyr Gly Val Gly Gln Gly Ser Gly Gln
1               5                   10                  15

<210> SEQ ID NO 40
<211> LENGTH: 9
<212> TYPE: PRT
<213> ORGANISM: Nephila pilipes

<400> SEQUENCE: 40

Gly Gly Gln Arg Gly Gln Gly Gly Gln
1               5

<210> SEQ ID NO 41
<211> LENGTH: 12
<212> TYPE: PRT
<213> ORGANISM: Nephila pilipes

<400> SEQUENCE: 41

Gly Gly Leu Gly Gly Tyr Gly Gly Gln Gly Gly Gln
1               5                   10

<210> SEQ ID NO 42
<211> LENGTH: 12
<212> TYPE: PRT
<213> ORGANISM: Nephila pilipes

<400> SEQUENCE: 42

Gly Gly Ile Gly Gly Ser Gly Gly Gln Gly Gly Gln
1               5                   10

<210> SEQ ID NO 43
<211> LENGTH: 12
<212> TYPE: PRT
<213> ORGANISM: Nephila pilipes

<400> SEQUENCE: 43

Gly Gly Leu Gly Gly Tyr Gly Gly Gln Gly Gly Gln
1               5                   10

<210> SEQ ID NO 44
<211> LENGTH: 15
<212> TYPE: PRT
<213> ORGANISM: Nephila pilipes

<400> SEQUENCE: 44

Gly Gly Leu Gly Gly Tyr Gly Gly Gln Arg Gly Gln Val Gly Gln
1               5                   10                  15
```

```
<210> SEQ ID NO 45
<211> LENGTH: 12
<212> TYPE: PRT
<213> ORGANISM: Nephila pilipes

<400> SEQUENCE: 45

Gly Gly Gln Gly Gly Ser Gly Gly Gln Gly Gly Gln
1               5                   10

<210> SEQ ID NO 46
<211> LENGTH: 5
<212> TYPE: PRT
<213> ORGANISM: Nephila pilipes

<400> SEQUENCE: 46

Ile Pro Ser Gly Ala
1               5

<210> SEQ ID NO 47
<211> LENGTH: 5
<212> TYPE: PRT
<213> ORGANISM: Nephila pilipes

<400> SEQUENCE: 47

Gly Pro Ser Gly Ser
1               5

<210> SEQ ID NO 48
<211> LENGTH: 5
<212> TYPE: PRT
<213> ORGANISM: Nephila pilipes

<400> SEQUENCE: 48

Arg Pro Ser Gly Ala
1               5

<210> SEQ ID NO 49
<211> LENGTH: 5
<212> TYPE: PRT
<213> ORGANISM: Nephila pilipes

<400> SEQUENCE: 49

Gly Pro Ser Gly Gln
1               5

<210> SEQ ID NO 50
<211> LENGTH: 5
<212> TYPE: PRT
<213> ORGANISM: Nephila pilipes

<400> SEQUENCE: 50

Arg Ser Ser Gly Ala
1               5

<210> SEQ ID NO 51
<211> LENGTH: 5
<212> TYPE: PRT
<213> ORGANISM: Nephila pilipes

<400> SEQUENCE: 51

Arg Pro Ser Gly Ile
1               5

<210> SEQ ID NO 52
<211> LENGTH: 5
```

```
<212> TYPE: PRT
<213> ORGANISM: Nephila pilipes

<400> SEQUENCE: 52

Arg Leu Ser Gly Ala
1               5

<210> SEQ ID NO 53
<211> LENGTH: 3
<212> TYPE: PRT
<213> ORGANISM: Nephila pilipes

<400> SEQUENCE: 53

Val Gly Gln
1

<210> SEQ ID NO 54
<211> LENGTH: 3
<212> TYPE: PRT
<213> ORGANISM: Nephila pilipes

<400> SEQUENCE: 54

Gly Gly Gln
1

<210> SEQ ID NO 55
<211> LENGTH: 3
<212> TYPE: PRT
<213> ORGANISM: Nephila pilipes

<400> SEQUENCE: 55

Leu Ala Gln
1

<210> SEQ ID NO 56
<211> LENGTH: 3
<212> TYPE: PRT
<213> ORGANISM: Nephila pilipes

<400> SEQUENCE: 56

Gly Ala Gln
1

<210> SEQ ID NO 57
<211> LENGTH: 3
<212> TYPE: PRT
<213> ORGANISM: Nephila pilipes

<400> SEQUENCE: 57

Asp Gly Gln
1

<210> SEQ ID NO 58
<211> LENGTH: 3
<212> TYPE: PRT
<213> ORGANISM: Nephila pilipes

<400> SEQUENCE: 58

Leu Ala Gly
1

<210> SEQ ID NO 59
<211> LENGTH: 3
<212> TYPE: PRT
<213> ORGANISM: Nephila pilipes
```

```
<400> SEQUENCE: 59

Ser Gly Gln
1

<210> SEQ ID NO 60
<211> LENGTH: 3
<212> TYPE: PRT
<213> ORGANISM: Nephila pilipes

<400> SEQUENCE: 60

Gly Thr Gln
1

<210> SEQ ID NO 61
<211> LENGTH: 3
<212> TYPE: PRT
<213> ORGANISM: Nephila pilipes

<400> SEQUENCE: 61

Gly Ala Gln
1

<210> SEQ ID NO 62
<211> LENGTH: 3
<212> TYPE: PRT
<213> ORGANISM: Nephila pilipes

<400> SEQUENCE: 62

Gly Pro Gly
1

<210> SEQ ID NO 63
<211> LENGTH: 3
<212> TYPE: PRT
<213> ORGANISM: Nephila pilipes

<400> SEQUENCE: 63

Ala Pro Gly
1

<210> SEQ ID NO 64
<211> LENGTH: 3
<212> TYPE: PRT
<213> ORGANISM: Nephila pilipes

<400> SEQUENCE: 64

Ala Pro Ser
1

<210> SEQ ID NO 65
<211> LENGTH: 7
<212> TYPE: PRT
<213> ORGANISM: Nephila pilipes

<400> SEQUENCE: 65

Gly Tyr Gly Thr Gly Ser Gly
1               5

<210> SEQ ID NO 66
<211> LENGTH: 5
<212> TYPE: PRT
<213> ORGANISM: Nephila pilipes

<400> SEQUENCE: 66
```

```
Gly Tyr Gly Ala Gly
1               5

<210> SEQ ID NO 67
<211> LENGTH: 7
<212> TYPE: PRT
<213> ORGANISM: Nephila pilipes

<400> SEQUENCE: 67

Gly Tyr Gly Gln Gly Ser Gly
1               5

<210> SEQ ID NO 68
<211> LENGTH: 7
<212> TYPE: PRT
<213> ORGANISM: Nephila pilipes

<400> SEQUENCE: 68

Gly Tyr Gly Ala Gly Ser Gly
1               5

<210> SEQ ID NO 69
<211> LENGTH: 6
<212> TYPE: PRT
<213> ORGANISM: Nephila pilipes

<400> SEQUENCE: 69

Gly Tyr Gly Gln Gly Ser
1               5

<210> SEQ ID NO 70
<211> LENGTH: 7
<212> TYPE: PRT
<213> ORGANISM: Nephila pilipes

<400> SEQUENCE: 70

Gly Tyr Gly Leu Gly Ser Gly
1               5

<210> SEQ ID NO 71
<211> LENGTH: 7
<212> TYPE: PRT
<213> ORGANISM: Nephila pilipes

<400> SEQUENCE: 71

Ala Thr Ile Ala Leu Thr Ala
1               5

<210> SEQ ID NO 72
<211> LENGTH: 7
<212> TYPE: PRT
<213> ORGANISM: Nephila pilipes

<400> SEQUENCE: 72

Ser Thr Ile Val Ile Thr Ala
1               5

<210> SEQ ID NO 73
<211> LENGTH: 7
<212> TYPE: PRT
<213> ORGANISM: Nephila pilipes

<400> SEQUENCE: 73

Thr Thr Ile Ala Leu Thr Ala
1               5
```

```
<210> SEQ ID NO 74
<211> LENGTH: 7
<212> TYPE: PRT
<213> ORGANISM: Nephila pilipes

<400> SEQUENCE: 74

Ser Thr Ile Ala Ile Thr Thr
1               5

<210> SEQ ID NO 75
<211> LENGTH: 7
<212> TYPE: PRT
<213> ORGANISM: Nephila pilipes

<400> SEQUENCE: 75

Thr Ala Ile Ala Ile Thr Ala
1               5

<210> SEQ ID NO 76
<211> LENGTH: 7
<212> TYPE: PRT
<213> ORGANISM: Nephila pilipes

<400> SEQUENCE: 76

Ser Thr Ile Ala Ile Thr Ala
1               5

<210> SEQ ID NO 77
<211> LENGTH: 7
<212> TYPE: PRT
<213> ORGANISM: Nephila pilipes

<400> SEQUENCE: 77

Ala Thr Ile Ala Ile Thr Ala
1               5

<210> SEQ ID NO 78
<211> LENGTH: 9
<212> TYPE: PRT
<213> ORGANISM: Nephila pilipes

<400> SEQUENCE: 78

Asn Ala Ala Ala Ala Asn Ala Ala Ala
1               5

<210> SEQ ID NO 79
<211> LENGTH: 5
<212> TYPE: PRT
<213> ORGANISM: Nephila pilipes

<400> SEQUENCE: 79

Ala Ala Ala Ala Ser
1               5

<210> SEQ ID NO 80
<211> LENGTH: 6
<212> TYPE: PRT
<213> ORGANISM: Nephila pilipes

<400> SEQUENCE: 80

Ala Ala Ala Thr Ala Ala
1               5

<210> SEQ ID NO 81
<211> LENGTH: 5
```

```
<212> TYPE: PRT
<213> ORGANISM: Nephila pilipes

<400> SEQUENCE: 81

Ala Ala Ala Ala Phe
1               5
```